United States Patent [19]

Vezjak

[11] Patent Number: 4,610,043

[45] Date of Patent: Sep. 9, 1986

[54] ORAL HYGIENE BRUSH

[76] Inventor: William Vezjak, 10549 Moorpark St., North Hollywood, Calif. 91602

[21] Appl. No.: 756,051

[22] Filed: Jul. 17, 1985

[51] Int. Cl.⁴ .............................................. A46B 9/04
[52] U.S. Cl. ..................................... 15/111; 128/304
[58] Field of Search ............. 15/111, 117, 110, 167 R, 15/227; 128/304, 62 A

[56] References Cited

U.S. PATENT DOCUMENTS

| | | | |
|---|---|---|---|
| 1,221,261 | 4/1917 | Worth | 15/111 |
| 1,891,864 | 12/1932 | Barrett | 128/304 |
| 2,049,956 | 8/1936 | Greenberg . | |
| 2,533,345 | 12/1950 | Bennett | 15/111 X |
| 4,328,604 | 5/1982 | Adams . | |
| 4,364,142 | 12/1982 | Pangle | 15/111 X |
| 4,455,704 | 6/1984 | Williams . | |

FOREIGN PATENT DOCUMENTS 335470  4/1921  Fed. Rep. of Germany .... 15/167 R

Primary Examiner—Peter Feldman
Attorney, Agent, or Firm—Christie, Parker & Hale

[57] ABSTRACT

A toothbrush and plaque scraper is disclosed for an oral cavity. A rigid handle, adapted to be grasped by a user, has a rigid base portion at a first end of a handle, extending away from the handle and having a top surface, at least one side surface and a bottom surface wherein the top, bottom and at least one side surface each comprise substantially uniform surfaces. Bristles are mounted to the top surface and adapted to be placed in the oral cavity for brushing teeth and extending in a first direction. A single rigid blade converges to an edge in a second direction substantially different from the first direction, contiguous to at least one of the at least one side surface and the bottom surface.

6 Claims, 5 Drawing Figures

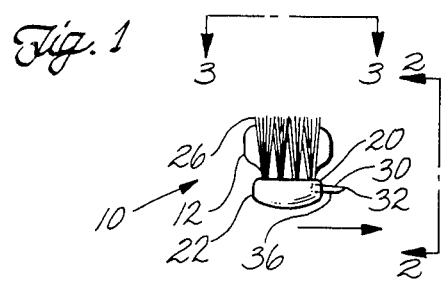
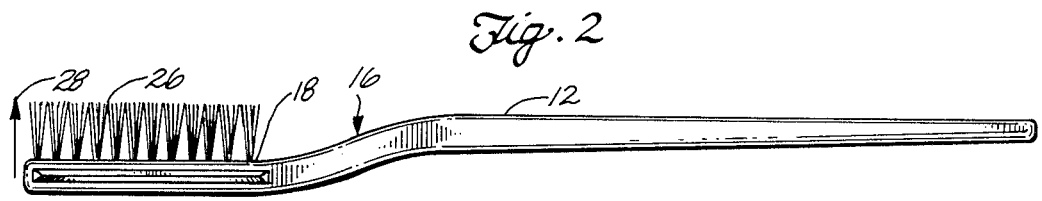
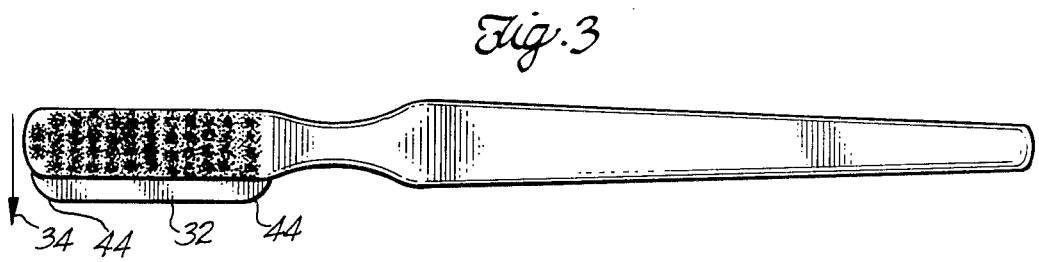
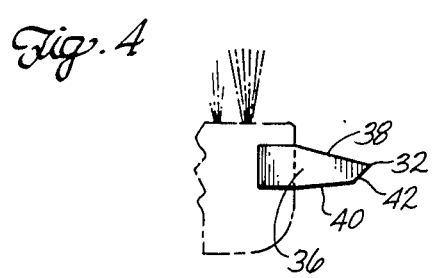
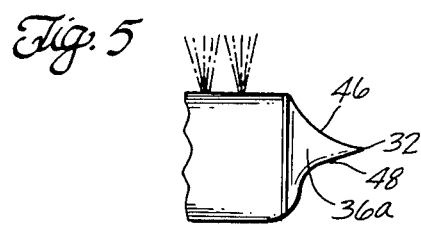

ORAL HYGIENE BRUSH

BACKGROUND OF THE INVENTION

1. Field of the Invention

The present invention relates to toothbrushes and more specifically, to combined toothbrush and plaque scrapers.

2. Description of Related Art

There are various instruments for maintaining oral hygiene, each of which has a particular function. A toothbrush is designed for brushing the teeth but is also used for brushing the gums and tongue to remove plaque. However, the bristles are not adequate for removing plaque from the tongue but for only for dislodging plaque from the tongue surface.

Greenberg, U.S. Pat. No. 2,049,956, shows a tongue-cleaning device in conjunction with a toothbrush. The tongue-cleaning device is located on the handle away from the bristles of the brush and therefore, necessitates changing the position of the hand on the brush to alternate between brushing the teeth and scraping the tongue with the scraper. Williams, U.S. Pat. No. 4,455,704, shows a toothbrush and tongue cleaner wherein the tongue cleaner is at the end of the toothbrush opposite the bristles. Bennett, U.S. Pat. No. 2,533,345, shows a toothbrush having tooth powder pickup grooves defined by a pair of lips used to scrape up the tooth powder from the hand.

SUMMARY OF THE INVENTION

A toothbrush and plaque scraper is disclosed for an oral cavity. A rigid handle, adapted to be grasped by a user, has a rigid base portion at a first end of a handle, extending away from the handle and having a top surface, at least one side surface and a bottom surface wherein the top, bottom and at least one side surface each comprise a substantially uniform surface. Bristles are mounted to the top surface and adapted to be placed in the oral cavity for brushing teeth and extending in a first direction. A single rigid blade converges to an edge in a second direction substantially different from the first direction, and is located contiguous to one of the at least one side surface and the bottom surface.

The rigid blade serves to remove plaque from the tongue by scraping with the edge of the blade. The rigidity of the blade assists in obtaining adequate removal of the plaque from the tongue. When the blade is oriented in a direction perpendicular to the direction in which the bristles extend, maximum leverage is obtained for scraping the tongue when the handle is held in the usual position for brushing the teeth. The blade extends a sufficient distance away from the base of the toothbrush so that the bristles and the edges of the base do not interfere with the removal of the plaque.

BRIEF DESCRIPTION OF THE DRAWINGS

FIG. 1 is a schematic and side elevation view of a toothbrush and plaque scraper in the form of a blade embodying the present invention;

FIG. 2 is a schematic and side elevation of the toothbrush of FIG. 1 taken along lines 2—2 of FIG. 1;

FIG. 3 is a schematic and top plan view of the brush and scraper taken along lines 3—3 of FIG. 1;

FIG. 4 is a schematic and side section of the blade of FIG. 1; and

FIG. 5 is a schematic and side section of a further embodiment of a blade for the toothbrush and scraper of FIG. 1.

DETAILED DESCRIPTION

The description of the apparatus herein incorporates a description of a method for using the apparatus.

FIGS. 1-3 show a toothbrush and plaque scraper 10 for brushing the teeth and scraping plaque from inside the oral cavity. The brush and scraper may be used for scraping plaque from the cheeks, the tongue and the gums. The brush and scraper is, therefore, necessarily dimensioned so that the brush and scraper fit into the mouth. The brush and scraper include a rigid handle 12 for being grasped by the user and for manipulating the brush and scraper. The rigid handle has a rigid base portion 14 at a first end 16 of the handle for supporting the brush and the scraper. The rigid base may be oriented with respect to the handle in any suitable fashion common to toothbrushes. For example, the base may be coplanar with the rigid handle or may be offset therefrom, as shown in FIG. 2.

The base 14 has a top surface 18, a first side surface 20 and a second side surface 22 each adjacent and on opposite sides of the top surface 18. A bottom surface 24 is opposite the top surface 18 and adjacent the first and second side surfaces of the base. The surfaces are substantially uniform and free of protrusions or obstructions, except as described below, for facilitating the use of the brush and scraper. The handle and base portions are made of any suitable materials but are preferably formed from a suitable plastic such as, for example, the plastic from which present toothbrushes are formed. Bristles 26 are mounted to the top surface 18 of the base and are adapted to be placed in the oral cavity for brushing teeth in the usual manner. The bristles extend in a first direction 28 perpendicular to and away from the top surface 18. The bristles are mounted or embedded in the base in the usual manner.

A single rigid blade 30 is mounted on or embedded in the first side surface 20 of the base portion 14 for scraping plaque. In an alternative embodiment, a single blade may be mounted on or embedded in each of the first and second sides so that the same brush style can be purchased by left handed people as well as right handed people. The blade may be glued or ultrasonically welded to the side surface 20 or may be embedded below the surface 20 of the base. If the blade is embedded, the blade may also be glued or ultrasonically welded to maintain the blade in place. Alternatively, the blade may be formed in a suitable molding or other plastic forming process, such as injection molding, to be integral with the base portion 14. Gluing or welding would then be unnecessary. The blade is made, preferably, from the same material from which the handle and base are formed. The blade is rigid so that the plaque can be scraped and removed from the tongue or other surface.

The blade converges to an edge 32 constituting the actual surface serving as the point of contact with the tongue. The blade extends in a second direction 34, preferably perpendicular to the first direction 28. As shown in FIG. 3, the blade is of constant width for essentially the entire length of the base. The blade extends from the first side surface 20 toward the edge and preferably has a pentagonal crossection 36 as shown is FIG. 4. The blade includes a top surface 38 sloping downwardly and away from the first side surface 20 toward the edge 32. The blade includes a bottom surface 40 extending substantially horizontally away from the first side surface 20 to a sloping surface 42 which slopes upwardly to meet the top surface 38 at the edge 32. This configuration provides structural integrity to the blade and a relatively sharp edge 32.

As shown in FIG. 5, the blade may be molded to form an edge 32 approximately ⅛ inch from the first side surface 20. The blade includes upper and lower concave surfaces 46 and 48, respectively, to help define the acute edge 32.

In another form of the invention, the blade 30 may extend in a direction opposite the first direction 28 from a midportion of the bottom surface 24. The blade would have the same structure and function as the blade 30 with respect to FIG. 1 but it is believed that this configuration would be somewhat more difficult to manipulate while scraping the tongue and is possibly more bulky in use.

As shown in FIG. 3, the ends 44 of the blade 30 are preferably rounded to eliminate any sharp corners that may otherwise result without the rounded edges.

The preferred dimensions of the blade 30 are as follows: The length of the base of the blade where it intersects the first side surface is 1.5 inches; the distance from the first side surface to an edge 32 is ⅛ of the inch; the distance from the second side surface to the edge 32 is approximately 9/16 of an inch; and the maximum height of the blade intersects the first side surface 20 is approximately 1/16 of an inch.

In using the brush and scraper to remove plaque from an inside surface of the oral cavity, the handle and base are rotated about a longitudinal axis to place the edge 32 in contact with the surface to be scraped. Preferably, the second direction 34 and therefore, the blade 30, is positioned normal to the surface to be scraped. The base 14 is then moved in a direction parallel to or opposite to the first direction 28 so that the edge 32 is scraped tangentially along the surface of the oral cavity. The handle and rigid base are manipulated as required to maintain the edge 32 oriented in a direction normal to the surface being scraped.

It should be noted that the above are preferred configurations but others are foreseeable. The described embodiments of the invention are only considered to be preferred and illustrative of the inventive concept; the scope of the invention is not to be restricted to such embodiments. Various and numerous other arrangements may be devised by one skilled in the art without departing from the spirit and scope of the invention.

What is claimed is:

1. A tooth brush and plaque scraper for a human oral cavity comprising:
   a rigid handle adapted to be grasped by a user;
   a rigid base portion at a first end of the handle, extending away from the handle and having a top surface, at least one side surface and a bottom surface wherein the top, bottom and at least one side surface each comprise substantially uniform surfaces;
   bristles mounted to the top surface wherein the base portion and the bristles are adapted to be placed in the oral cavity for brushing teeth and wherein the bristles extend in a first direction; and
   a single rigid blade converging to a relatively sharp, pointed scraping edge in a second direction substantially perpendicular to the first direction contiguous to the at least one side surface, the scraping edge having a constant width in the second direction for essentially the entire length of the base portion.

2. The brush and scraper as claimed in claim 1 wherein the base portion comprises a first material and the rigid blade comprises a second material wherein the first and second materials are substantially the same.

3. The brush and scraper as claimed in claim 1 wherein the rigid blade comprises means wedged into the rigid base.

4. The brush and scraper as claimed in claim 1 wherein the rigid blade comprises a substantially quadrilateral cross section.

5. The brush and scraper as claimed in claim 2 wherein the rigid handle and the rigid blade comprise plastic.

6. The brush and scraper as claimed in claim 1 wherein the blade comprises a length of approximately 1.5 inches.

* * * * *